United States Patent [19]
Hirabayashi et al.

[11] Patent Number: 4,877,402
[45] Date of Patent: Oct. 31, 1989

[54] ARTIFICIAL TOOTH CROWN AND METHOD OF PRODUCING THE SAME

[75] Inventors: Masaya Hirabayashi; Iwao Noda, both of Shiga, Japan

[73] Assignee: Kyocera Corporation, Kyoto, Japan

[21] Appl. No.: 217,145

[22] Filed: Jul. 1, 1988

Related U.S. Application Data

[63] Continuation of Ser. No. 922,825, Oct. 22, 1986, abandoned, which is a continuation of Ser. No. 654,654, Sep. 25, 1984, abandoned.

[30] Foreign Application Priority Data

Sep. 26, 1983 [JP] Japan ................................ 58-178962

[51] Int. Cl.⁴ .............................................. A61C 5/08
[52] U.S. Cl. .................................. 433/218; 433/222.1; 106/35
[58] Field of Search ...................... 433/215, 218, 222.1, 433/223, 228.1; 264/16; 106/35

[56] References Cited

U.S. PATENT DOCUMENTS

| | | | |
|---|---|---|---|
| 2,480,048 | 8/1949 | Rice | 264/19 |
| 2,724,166 | 11/1955 | Myerson | 264/19 |
| 3,649,608 | 3/1972 | Logemann | 525/228 |
| 3,787,900 | 1/1974 | McGee | 106/35 X |
| 3,913,229 | 10/1975 | Driskill et al. | 433/228.1 X |
| 3,922,155 | 11/1975 | Broemer et al. | 65/33 |
| 3,981,736 | 9/1976 | Broemer et al. | 501/10 |
| 4,028,325 | 6/1977 | King et al. | 523/115 |
| 4,097,935 | 7/1978 | Jarcho | 433/228.1 X |
| 4,113,500 | 9/1978 | Ebihara et al. | 501/1 |
| 4,131,597 | 12/1978 | Bluethgen et al. | 523/114 |
| 4,149,893 | 4/1979 | Aoki et al. | 433/228.1 X |
| 4,308,064 | 12/1981 | Takami et al. | 433/228.1 X |
| 4,321,042 | 3/1982 | Scheicher | 433/201 |
| 4,439,959 | 2/1984 | Faunce | 433/222 X |
| 4,451,235 | 5/1984 | Okuda et al. | 433/202 X |
| 4,475,892 | 10/1984 | Faunce | 433/212 |
| 4,481,036 | 11/1984 | Panzera | 433/202 X |
| 4,503,157 | 3/1985 | Hatahira | 433/201 X |
| 4,547,327 | 10/1985 | Bruins et al. | 264/16 |
| 4,562,882 | 1/1986 | Alleluia | 164/529 |

FOREIGN PATENT DOCUMENTS

51-8970 3/1976 Japan .
191252 11/1982 Japan .

Primary Examiner—Nancy A. B. Swisher
Attorney, Agent, or Firm—Spensley Horn Jubas & Lubitz

[57] ABSTRACT

The disclosure relates to an artificial tooth crown composed of glass ceramics comprising crystallized calcium phosphate forming essentially apatite which is a main inorganic component of natural bones or teeth. The disclosure also relates to a method of producing the artificial tooth crown. The artificial tooth crown has superior dimensional accuracy since it is made by precision casting. The tooth crown can be securely adhered by a dental cement such as glass ionomer. Furthermore, the physical properties of the tooth crown are very similar to those of the natural teeth, and the wear caused by the biting motion between the tooth crown and its mating tooth does not differ from that caused by the biting motion between the natural teeth. Furthermore, the method does not differ from the conventional precision casting method.

11 Claims, 2 Drawing Sheets

ARTIFICIAL TOOTH CROWN AND METHOD OF PRODUCING THE SAME

This is a continuation of application Ser. No. 06/922,825 filed on Oct. 22, 1986, now abandoned, which in turn is a continuation of application Ser. No. 06/654,654 filed on Sept. 25, 1984, now abandoned.

BACKGROUND OF THE INVENTION

1. Field of the Invention

The present invention relates to an artificial tooth crown made of glass ceramics (recrystalized glass), i.e., calcium phosphate-based minerals forming essentially apatite, and a method of producing the artificial tooth crown.

2. Prior Art

The conventional artificial tooth (hereinafter, refer to merely as "crown") crowns are classified into four types. The first type is made of metal, the second type is made of porcelain (jacket crown), the third type is made of a combination of metal and porcelain (metal bond) and the fourth type is made of a combination of metal and resin. The crown of the first type made of precious metal, semi-precious metal or nonprecious metal can have a highly precise shape by precision casting. However, the crown made of precious or semi-precious metal is expensive and the luster inherent in such metal does not match well with the living body and is disliked. In the case of the crown made of nonprecious metal, the harm of nonprecious metal to the living body has been reduced considerably by the improvement of metal qualities but has not yet been completely eliminated. The second type is produced by a repeatedly building and firing porcelain. Therefore, the dimensions of the crown produced in this way may be changed by repeated heat application, thus it may not properly fit to natural teeth. Accordingly, the yield rate of this type is extremely low since it needs high technology of porcelain building and firing and must have high dimensional accuracy, resulting in high production cost.

In the case of the third type made of a combination of metal and porcelain, porcelain is built and baked on the crown surface to shade the luster of the matal crown. In this case, the problems regarding the first type will also arise, and its production is complicated and requires high cost. Furthermore, the metal crown is not harder than the opposed natural tooth and thus it is locally corroded or deformed by biting motion for an extended period. On the contrary, the crown made of or coated with porcelain is harder than the natural tooth and wears out the opposed natural tooth. In addition, dimensional accuracy drops due to repeated heat treatment as described above. The fourth type made of a combination of metal and resin is apt to discolor and fatigue easily. That is, the fourth type is not durable due to deterioration after use for an extended period.

SUMMARY OF THE INVENTION

It is therefore an object of the present invention to solve the above-mentioned problems, more particularly to produce an artificial crown using grass ceramics comprising crystalized calcium phosphate minerals forming essentially apatite which is a main inorganic component of natural bones and teeth. Although the crown is made of ceramics, since it is made by precision casting, it has an extremely high dimensional accuracy and can be precisely mounted on a natural tooth. The crown can be firmly adhered to the natural tooth when a cement (glass ionomer or carboxylate for example; these are commercially available) having a good chemical bonding strength with calcium phosphate is used. In addition, since the physical properties of the glass ceramics are extremely similar to those of the natural tooth, the wear of the crown due to occlusal motion with the opposed natural tooth makes no great difference with the wear due to biting stress between the natural teeth. The mechanical strength of the crown is the same rank as that of the natural teeth. Furthermore, the crown can be made easier in shorter time than porcelain crowns. Therefore, the crown is far less expensive. This invention has the following advantages in terms of its production method. Since the conventional dental precision casting apparatus can be used without marked modifications, accurate dimensions can be obtained easily without special production technology and apparatuses. Moreover, the crown can be easily colored. The objects will become more apparent when preferred embodiments of the present invention are taken in connection with the drawings.

DETAILED DESCRIPTION OF THE PREFERRED EMBODIMENTS

Figure 1:
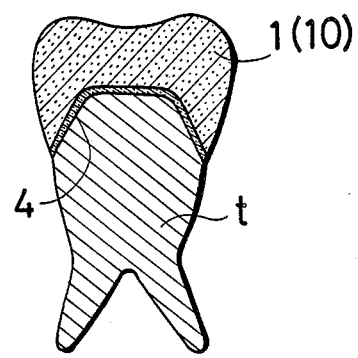
FIG. 1 is a vertical sectional view of a single crown of an embodiment of the present invention.

The glass ceramic compositions disclosed in the Japanese Patent Publication 51-8,970 and the Japanese Patent Provisional Publication (Kokai) 57-191,252 for example may be applied to the raw materials of the glass ceramic composition of the present invention. Both are made of glass ceramics composition based on $MgO-CaO-SiO_2-P_2O_5$ and have similar composition ranges. Both materials comprise microcrystals of apatite (oxy-apatite $[Ca_{10}(PO_4)_6O]$ or fluoro-apatite $[Ca_{10}(PO_4)_6F_2]$ for example) which are similar to hydroxy-apatite $[Ca_{10}(PO_4)_6(OH)_2]$, the basic material of the natural teeth. When they are used for artificial bones and dental roots, they have stronger bonding with living bones than other conventional materials. The latter one crystalizes wallastonite $(CaO.SiO_2)$ precipitate simultaneously with apatite for higher strength. This invention considered to be novel in the fact that glass ceramics comprising mainly the crystals of apatite and occasionally other calcium phosphate minerals such as tricalcium phosphate $(3CaO.P_2O_5)$ is used for the artificial tooth crown which has effects and objects different from those of implant members. In other words, an important point of the use of the ceramics is not to strengthen the bonding with the living bones but to provide harmonious occlusal abrasion so that the biting surfaces of the crown and its opposed natural tooth are not excessively damaged after the mutual biting motion, that is, to provide the crown having the physical properties similar to those of the natural teeth. The present invention also provides a method of efficiently producing the glass ceramic crown with high dimensional accuracy by forming the crown using an ordinary dental precision casting (centrifugal or pressure casting) apparatus without marked modifications (crystalization of calcium phosphate minerals is carried out in the casting process, however). These ideas have not yet been disclosed by the above publications and are peculiar to the present invention. Unlike the implant members embedded in the living bones, which are subjected to various external forces, such as compression, bending, impact, tension and shearing, the crown, regardless of a crown or a bridge is mainly subjected to compression and bending stresses. The superior physically properties inherent in the ceramics can cope with the compression stress. The ceramics with a bending strength of approximately 1,000 kg/cm$^2$ can sufficiently cope with the bending stress caused during daily use. It has been recognized that the embodiment of the present invention has this bending strength even when wollastonite has not been crystalized. Therefore, unlike the latter invention of the prior art, it is not necessary to contain wollastonite. Uneven crystalization of wollastonite generates cracks in the casted product and may damage the product.

Therefore, with the present invention, the crystalization temperature is maintained between 800° C. to 900° C. after casting to prevent excessive crystalization of wollastonite and to essentially crystalize apatite. In addition to apatite, tricalcium phosphate and other calcium phosphate minerals can also be used as minerals of the present invention. Those minerals are secondary products generated according to temperature conditions for crystalization of apatite. Therefore, both the glass ceramic compositions of the former and latter prior art inventions can be used. In other words, various glass ceramics materials comprising microcrystals of calcium phosphate minerals mainly composed of apatite can be used as the ceramics of the present invention as long as they are castable. The apatite microcrystals of the present invention should be 30% or more of the entire ceramics by volume; preferably 50% or more. If the percentage is lower than 30%, the improvement of the physical properties by the crystalization of the microcrystals is reduced.

The artificial tooth crown of the present invention is detailed as follows by taking its production method as an example.

(a) Preparation of raw material of glass ceramic composition

Prepare a batch equivalent to glass composition based on $SiO_2$—$P_2O_5$—$CaO$—$MgO$—$CaF_2$ using oxides, hydrates or fluorides. The generated composition is heated, melted and vitrificated using a crucible made of a nonactive material such as platinum in a furnace (electric furnace). The glass melt is then rapidly cooled to a normal temperature while the glass state is maintained. If it is cooled gradually, some microcrystals of the above-mentioned minerals begins to precipitate and the melting temperature may be elevated improperly when it is reheated later.

(b) Casting

The glass melt is melted again in the furnace at 1,200°–1,300° C. under a reduced pressure. Pressure should be reduced by approximately 100 mmHg to prevent bubbles from entering the glass melt. The investment material for the casting mold should be made of a material having a coefficient of thermal expansion similar to that of the above-mentioned glass material. This is necessary to prevent thermal stress between the mold and the poured material when the material is heated in the succeeding process for crystalization. In actual practice, magnesium phosphate, magnesia or zirconia is used. If the glass melt is poured in a cool casting mold, the poured glass is subjected to an undesirable stress. To prevent this stress, the mold should be heated to an appropriate temperature (700° C. for example). Furthermore, pressure should be reduced to prevent bubbles from entering the mold when the glass melt is poured. The normal centrifugal casting or pressurized casting can be used.

(c) Crystalization

After the glass melt obtained at step (b) is poured into the mold and subjected to a required centrifugal force or pressure, the mold including the glass melt is heated to the crystalization temperature of the apatite mineral (800°–900° C.) for one or two hours. If it is necessary to crystalize a great deal amount of wollastonite as in the case of the latter one of the prior art inventions, the mold should be heated at 1,000° C. or more. In the case of the present invention, however, the crystalization of wollastonite should be avoided since crystalized wollastonite may damage the casted product. In other words, the mold should be heated up to 800°–900° C. which is the temperature range where apatite is mainly crystalized. By this heating, microcrystals composed of apatite and similar materials such as tricalcium phosphate are dispersed in glass. Usually the microcrystals are evenly distributed on the surface of the casted product. As a result, an artificial crown with the physical properties close to those of the natural teeth can be obtained on the surface. The material will slightly expand when the microcrystals are produced. In the case of the present invention, the expansion is prevented by the casting mold surface since the investment material having the coefficient of thermal expansion close to that of the glass material is used and the mold including the poured material is heated for crystalization without removing the casted product from the mold. Accordingly, a precompression stress is applied to the casted product. Thus the mechanical strength of the produced artificial crown is improved and can have high dimensional accuracy.

The artificial crown produced in this way has a semitransparent base color of glass ceramics. It has a linear expansion coefficient of $9-11\times10^{-6}/°C.$ (800° C.), a bending strength of 1,200–1,400 kg/cm$^2$ and a compression strength of 9,000–10,000 kg/cm$^2$. These properties of the crown are similar to those of hydroxy apatite. The crown is also stable against the effects of saliva, acid and alkali at the interior of the mouth. Since the crown is semitransparent, a color tone similar to and harmonized with the color of the natural teeth can be obtained by coloring only the inside of the crown using a desired coloring agent.

The method of casting the crown of the invention featuring high productivity and low cost has been described above to produce the artificial crown. However, the tooth crown of the present invention can also be produced by powder compression forming and sintering. That is, powder (fine powder is desirable in this case) of the raw material of glass ceramic prepared at step (a) is pressed and formed into the desired crown shape, sintered at a sintering temperature and, if necessary, heated for crystalization. Although this dry method has lower productivity and requires higher cost, it is technically similar to the casting method.

Figure 2:
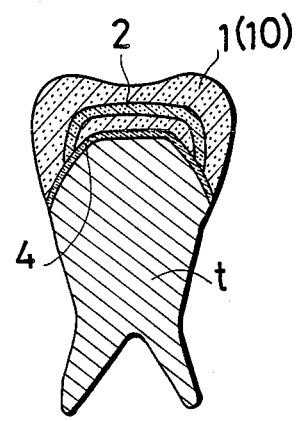
FIG. 2 (A) and (B) are vertical sectional views of a single crowns of another embodiment of the present invention.
Figure 2:
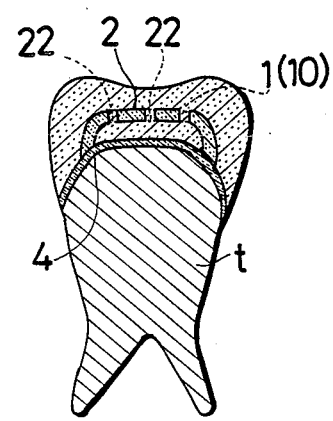
Figure 3:
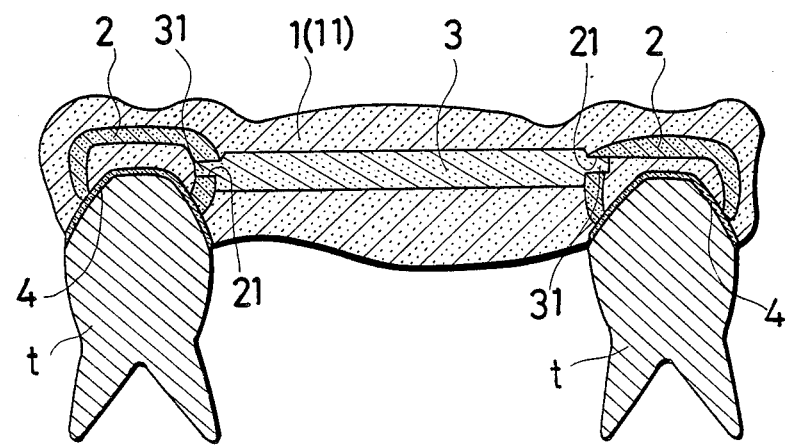
FIG. 3 (A) and (B) are vertical sectional views of a bridge of the present invention.
Figure 3:
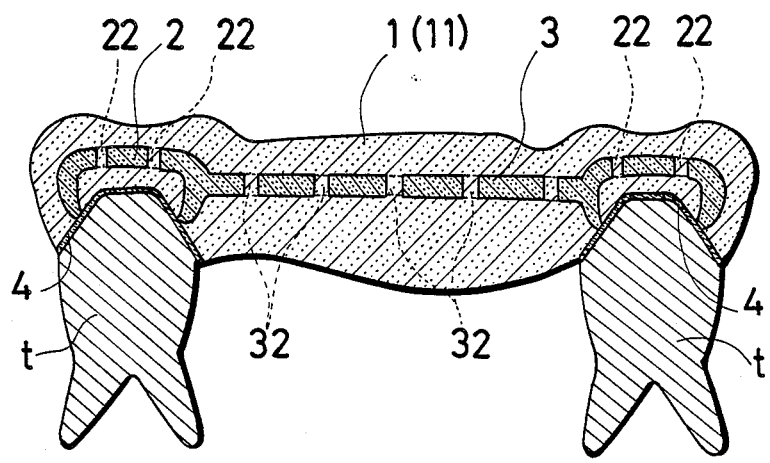
Figure 4:
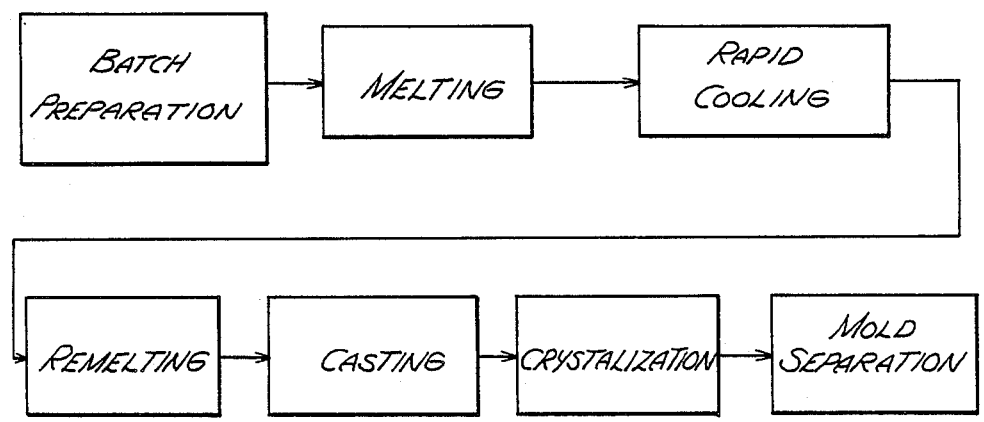
FIG. 4 shows the flowchart of the production method of the present invention.

The actual construction of the crown of the present invention is described below referring to FIGS. 1, 2 and 3. FIG. 1 shows an embodiment of a single crown. The impression of the upper surface of a natural tooth t is taken, the corresponding casting mold is formed by the lost wax process, and a single crown 10 is casted. The adhesion between the natural teeth t and the crown 10 can be greatly improved by using a cement 4, such as glass ionomer cement or carboxylate cement which has superior adhesion performance to apatite. The crown shown in FIG. 2 (A) and (B) are similar to that shown in FIG. 1. However, the first reinforcing member piece 2 with a reversed bowl shape is embedded an integrated in the crown 10 vertical to the occlusal direction to provide higher resistance against external biting forces. The member piece 2 has the expansion coefficient similar to that of the mono crown 10 and is made of alumina ($Al_2O_3$) ceramics or zirconia ($ZrO_2$) ceramics which is chemically inactive with the monocrown 10. The former one has a linear expansion coefficient of $8 \times 10^{-6}/°$ C. (800° C; omitted hereafter) and the latter one has $11 \times 10^{-6}/°$ C. These are similar to that of the glass ceramics, that is, $10 \times 10^{-6}/°$ C. They are chemically inactive. Instead of these ceramic materials, metal Pd (a linear expansion coefficient of $11 \times 10^{-6}/°$ C.), Pd alloy or metal Ti (a linear expansion coefficient of $9 \times 10^{-6}/°$ C.) or Ti alloy can also be used. The first reinforcing member piece 2 of the present embodiment can be formed separately in the desired shape and embedded in the crown 10 when the ceramics is casted. Although the first reinforcing member piece 2 shown in FIG. 2 (A) is a solid strip, the reinforcing member piece 2 shown in FIG. 2 (B) has plural through holes 22 in the direction of the thickness. An anchoring effect is obtained by passing glass ceramics 1 through the through holes. In addition, the weight of the strip is reduced. The crown 1 shown in FIG. 3 (A) and (B) is a bridge 11. In addition to the first reinforcing member piece 2 which is the same as that shown in FIGS. 2 (A) and 2 (B), the second reinforcing member piece 3 is used in this embodiment to increase the bending strength of the span section of the bridge 11. Although the member piece 3 is made of the same material so that of the member piece 2, it has a shape of a rod or a strip. When the reinforcing member pieces 2 and 3 are made of ceramics, the projections 31 provided at both ends of the member piece 3 as shown in FIG. 3 (A) are inserted into the through holes 21 provided in the two member pieces 2. As a result, the two member pieces 2 are connected with the member piece 3. These connected pieces are embedded in and integrated with the bridge 11. When the reinforcing member pieces 2 and 3 are made of metal, they can be casted into a single piece as shown in FIG. 3 (B). As can be understood by the embodiment shown in FIG. 3, the bending strength of the span is increased and thus the bridge can have higher durability. Like the above-mentioned embodiment, it is desirable to provide the through holes 22 and 32 at the appropriate positions of the reinforcing member pieces as shown in FIG. 3 (B) so that the anchoring effect by glass ceramics is obtained and the weight is reduced.

Having described the five embodiments, it is obvious that the present invention is not limited to these embodiments but the number of the reinforcing member pieces and their shapes and constructions can be modified.

Since the glass ceramics is semitransparent, it is not always necessary to color the entire crown. The color tone similar to the natural teeth can be obtained by baking an appropriate coloring agent on only the inside (the side contacting the dental cement 4) of the crown 1 or by properly coloring the cement 4. When the first and second reinforcing member pieces 2 and 3 are used, they should be colored on their entire surfaces using the above-mentioned coloring agent during their production processes. By this coloring, the reinforcing member pieces can provide a natural tone color when they are looked at from the outside. Therefore, the crown of the present invention can have small coloring area and can be colored easily. The production example of the present invention and its results and prosthesis are described below.

(PRODUCTION EXAMPLE)

(a) Preparation of raw material of glass ceramic composition

The batch having the composition of $SiO_2$ 27% (weight percent; omitted hearafter), $P_2O_3$ 13%, CaO 54%, MgO 3%, $B_2O_3$ 2% and $CaF_2$ 1% was prepared using oxides, hydrates or fluorides. The batch was put into a platinum crucible and the crucible was heated at 1,450° C. for two hours in an electric furnace to melt the composition. Then the glass melt was rapidly cooled to form glass ceramic composition.

(b) Casting

The composition produced at step (a) was melted at 1,300° C. in the electric furnace. A centrifugal casting mold made of magnesium phosphate investment material was heated at 700° C. The glass melt was poured under a reduced pressure in the casting mold and centrifugal casting was done. The casted product was the single crown shown in FIG. 1.

(c) Crystalization

The heated product in the casting mold, which was obtained in step (b), was further heated at 800° C. for two hours to crystalize a great deal amount of oxy-apatite $[Ca_{10}(PO_4)_6O]$.

(d) Mold separation

The mold was separated from the casted product after the crystalization had been completed.

(Result and prosthesis)

The obtained glass ceramics showed the following mechanical properties: a linear expansion coefficient of $10 \times 10^{-6}/°$ C. (800° C.), a bending strength of 1,400 $kg/cm^2$ and a compression strength of 9,000 $kg/cm^2$. It was semitransparent. An ivory coloring agent (stain) having the color of the natural teeth was baked on the inside of the crown. Then the crown was mounted and secured on the natural tooth using the glass ionomer cement. The artificial tooth crown produced in this way has a color similar to that of the natural teeth. It did not damage the opposed natural tooth even after use for an extended period (approximately 12 months) and had no abnormalities on its biting surface.

As clearly understood by the above description, the artificial tooth crown of the present invention has the following superior advantages. Since the artificial tooth crown of the present invention is made of glass ceramics comprising microcrystals of calcium phosphate minerals similar to the natural teeth, the physical properties of this artificial tooth crown are close to those of the natural teeth. The occlusal surface of the crown is not hardly worn and that of the opposed tooth is not damaged, thus the crown can be used for an extended period. Furthermore, the crown can be securely adhered to the natural tooth using a cement having a good affinity with apatite such as glass ionomer. Moreover, since the glass ceramics is semitransparent, the crown has a color similar to the natural tooth by applying the desired color to its inside. Therefore, harmonious color coordination is obtained and coloring is easy.

This method of producing the crown according to the present invention uses castable glass ceramics so that the conventional dental casting method can be used without marked modifications. As a result, products with high dimensional accuracy can be easily produced efficiently at low cost. In addition, calcium phosphate is microcrystalized while the composition remains in the casting mold to prevent volumetric expansion due to crystalization. As a result, the dimensions of the product can be accurate, and precompression stress can be applied to the product.

Having described our invention as related to the embodiments shown in the accompanying drawings, it is out intention that the invention be not limited by any of the details of description, unless otherwise specified, but rather be construed broadly within its spirit and scope as set out in the accompanying claims.

We claim:

1. An artificial tooth crown for attachment to a tooth of a dental patient, comprising a body consisting of a glass ceramic, wherein said glass ceramic comprises a generally transparent glass matrix and at least 30% by volume of crystallized calcium phosphate crystals, said body being prepared by casting followed by crystallization at a temperature of between about 800° and 900° C.

2. An artificial tooth crown according to claim 1, wherein said glass ceramic is based on $SiO_2$—$P_2O_5$—$CaO$—$MgO$ and $CaF_2$.

3. An artificial tooth crown according to claim 2, wherein said glass ceramics has a linear expansion coefficient of $9-11 \times 10^{31} 6/°$ C.

4. An artificial tooth crown according to claim 2, wherein a first reinforcing member piece comprising ceramics or metal and having an expansion coefficient similar to that of said glass ceramic is embedded almost vertical to an occlusal direction.

5. An artificial tooth crown according to claim 4, wherein said first reinforcing member has at least one transverse through hole and said glass ceramic passes therethrough.

6. An artificial tooth crown according to claim 4, wherein said first reinforcing member comprises alumina or zirconia ceramics.

7. An artificial tooth crown according to claim 4, wherein said first reinforcing member comprises a metal selected from the group consisting of Pd, Pd alloys, Ti and Ti alloys.

8. An artificial tooth crown according to claim 4, further comprising a second reinforcing member piece comprising ceramics or metal and having an expansion coefficient similar to that of said glass ceramic, wherein said second reinforcing member piece is embedded almost vertical to an occlusal direction.

9. An artificial tooth crown according to claim 8, wherein said second reinforcing member has at least one transverse through hole and said glass ceramic passes therethrough.

10. An artificial tooth crown according to claim 8, wherein said second reinforcing member comprises alumina or zirconia ceramics.

11. An artificial tooth crown according to claim 8, wherein said second reinforcing member comprises a metal selected from the group consisting of Pd, Pd alloys, Ti and Ti alloys.

* * * * *